June 3, 1975 H. H. KURAMOTO Plant Pat. 3,725
ROSE PLANT
Filed Feb. 25, 1974
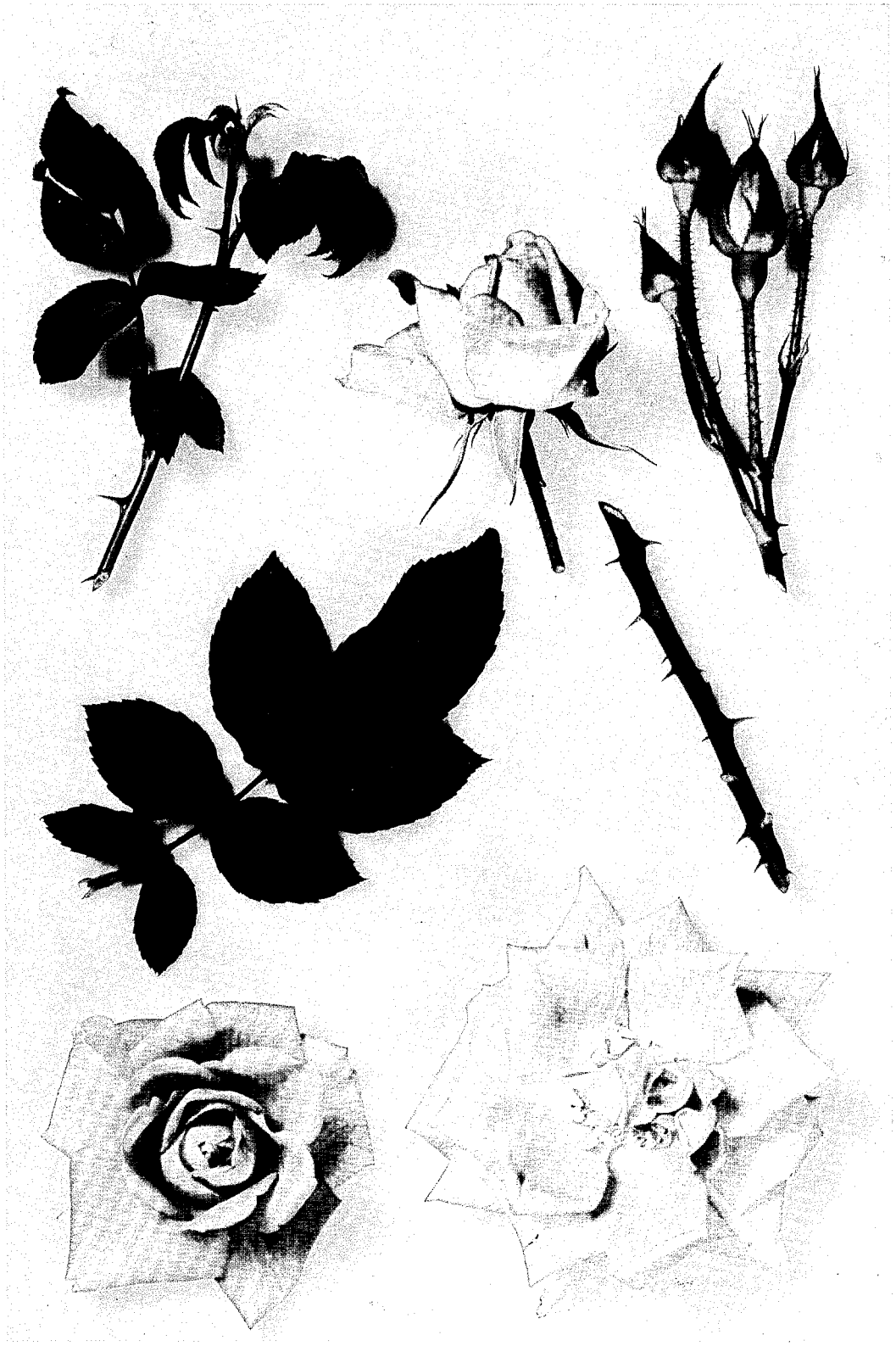

United States Patent

Plant Pat. 3,725

Patented June 3, 1975

3,725

ROSE PLANT

Hideharu Henry Kuramoto, Salinas, Calif., assignor to Jackson & Perkins Company, Medford, Oreg.

Filed Feb. 25, 1974, Ser. No. 445,573

Int. Cl. A01h *5/00*

U.S. Cl. Plt.—22 1 Claim

This present invention relates to a new and distinct cultivar of rose plant of the floribunda class which was discovered by me as a sport of the cultivar Woburn Abbey, Plant Pat. 2,319.

This discovery was made in a greenhouse bench planted to the cultivar Woburn Abbey in my greenhouse in San Lorenzo, Calif. While cutting cut flowers from the bench of cultivar, Woburn Abbey, I noticed one bud of a different color than the normal color of Woburn Abbey. Propagation of the budding eyes of this one stem indicated that this was a sport of the parent cultivar and further propagation proved that the sport came true through succeeding propagations.

This new cultivar is substantially identical in all respects to its parent, except that the bud and flower color do not have the yellow underside of the petals. The lower side of the petal is nearly the same color as the upper side.

The following is a detailed description of my new rose variety with color terminology in accordance with Color Standards and Nomenclature, Ridgway, except where ordinary dictionary significance of color is indicated.

Parentage:
- *Sport.*—Sport of Woburn Abbey, U.S. Plant Pat. 2,319.

Classification:
- *Botanical.*—Rosa hybrid.
- *Commercial.*—Floribunda.

FLOWER

Observations were made at Irvine, Calif., in late September 1973.

Blooming habit: Recurrent—continuous.

Bud:
- *Size.*—1 inch when petals start to unfurl.
- *Form.*—Blunt top, broad base.
- *Color.*—Between Grenadine Red and Mars Orange, Plate II, lightening to Light Orange Yellow, Plate III, at petal base. When half blown; inside of petals between Grenadine Red and Mars Orange, Plate II; reverse of petals only slightly lighter than upper side of petals with underlying tints of near Light Orange Yellow, Plate III; predominant color being between Grenadine Red and Mars Orange, Plate II.
- *Sepals.*—Color: outer surface Spinach Green, Plate 5, also with many stipitate glands. Inner surface light Cress Green, Plate 31. Three appendaged sepals lightly appendaged. Two unappendaged sepals slightly hairy edged.
- *Receptacle.*—Color—Spinach Green, Plate 5. Shape—funnel. Size—long. Surface—smooth.
- *Peduncle.*—Length—medium. Surface—prickly. Color—light green. Strength—still, erect.
- *Opening.*—Petals slightly curled.

Bloom:
- *Size.*—Medium. Average size when fully expanded 3½".
- *Borne.*—Singly and several together.
- *Stems.*—Long and medium.
- *Form.*—When first opened, cupped. Permanence—outer petal edges slightly curled.
- *Petalage.*—Number of petals under normal conditions—25.

- *Color.*—Center of flower: Upper side of petals between Grenadine Red and Mars Orange, Plate II. Reverse side of petals only slightly lighter than upper side of petals. Outer petals: Upper side of petals between Grenadine Red and Mars Orange, Plate II. Reverse of petals only slightly lighter than upper side of petals. Base of petals—large area of color near Light Orange Yellow, Plate II. General tonality from a distance between Grenadine Red and Mars Orange, Plate II.
- *Discoloration.*—General tonality at end of first day—same. Third day—slightly lighter than freshly opened flower.
- *Fragrance.*—Moderate.
- *Petals.*—Textured: leathery.
- *Surface.*—Inside—satiny. Reverse—shiny.
- *Shape.*—Broad and round.
- *Form.*—Edges slightly quilled.
- *Arrangement.*—Imbricated.
- *Petaloids in center.*—Few, small.
- *Persistence.*—Drop off cleanly.
- *Lastingness.*—On the plant—long. As cut flower—very long.

Reproductive parts:
- *Anthers.*—Medium. Color—yellow. Arrangement—regular around styles.
- *Filaments (threads.)—Medium. Color—yellow.*
- *Pollen.*—Lemon yellow.
- *Styles.*—Loosely separated of uneven lengths.
- *Stigmas.*—Color—orange to buff.
- *Ovaries.*—All enclosed in calyx.

Fruit: (Not observed).

Plant:
- *Form.*—Bush.
- *Growth.*—Vigorous, upright.

Foliage:
- *Size.*—Medium.
- *Quantity.*—Normal.
- *Color.*—New foliage—Upper side—Yellowish Oil Green, Plate 5. Under side—Citrine, Plate 4. Old foliage—Upper side—Spinach Green, Plate 5. Under side—Light Bice Green, Plate 17. Number of leaflets on normal mid-stem leaves—5 or 7.

Leaflets:
- *Shape.*—Oval pointed.
- *Texture.*—Leathery. Under side—smooth. Ribs and veins—ordinary.
- *Edge.*—Serrated.
- *Serration.*—Single.
- *Petiole.*—Rachis—Color — reddish. Underside—prickles.
- *Stipules.*—Short and smooth.

Wood:
- *New Wood.*—Yellowish Olive, Plate 30. Bark—smooth.
- *Old Wood.*—Cress green, Plate 31. Bark—smooth.

Prickles:
- *Quantity.*—On main stalks from base—ordinary. On laterals from stalk—ordinary.
- *Form.*—Narrow base. Long, hooked slightly downward.
- *Color when young.*—Old rose, Plate 13.
- *Position.*—Irregular.

Small prickles:
- *Quantity.*—None on main stalks. None on laterals.

The accompanying drawing shows typical specimens of the vegetative growth and flowers of this new cultivar in different stages of development depicted in color as nearly true as is reasonably possible to make the same in a color illustration of this character.

I claim:

1. A new and distinct cultivar of rose plant of the floribunda class, substantially as herein shown and described, characterized particularly as to novelty by being substantially identical with its parent cultivar, Woburn Abbey, U.S. Plant Pat. 2,319, but being distinguished therefrom by its flower color of between Grenadine Red and Mars Orange on both sides of the petals.

No references cited.

ROBERT E. BAGWILL, Primary Examiner